United States Patent [19]

Harper et al.

[11] Patent Number: 5,183,933
[45] Date of Patent: Feb. 2, 1993

[54] PROCESS FOR PREPARING 2,6-NAPHTHALENE-DICARBOXYLIC ACID

[75] Inventors: Jon J. Harper; George E. Kuhlmann, both of Naperville; Keith D. Larson, Chicago; Rosemary F. McMahon, Wheaton; Paul A. Sanchez, Lisle, all of Ill.

[73] Assignee: Amoco Corporation, Chicago, Ill.

[21] Appl. No.: 776,812

[22] Filed: Oct. 15, 1991

[51] Int. Cl.$^5$ ............................................. C07C 51/265
[52] U.S. Cl. ...................................... 562/414; 502/28; 556/49; 556/147; 562/416; 562/417; 562/487; 562/488
[58] Field of Search ............... 562/416, 414, 417, 487, 562/488; 502/28; 556/49, 147

[56] References Cited

U.S. PATENT DOCUMENTS

| | | | |
|---|---|---|---|
| 3,856,855 | 12/1974 | Yamashita et al. | 562/416 |
| 3,870,754 | 3/1975 | Yamashita et al. | 562/416 |
| 4,490,298 | 12/1984 | Feld | 562/412 |
| 4,587,355 | 5/1986 | Brown et al. | 562/414 |
| 4,769,488 | 9/1988 | Nowicki et al. | 562/414 |
| 4,786,752 | 11/1988 | Holzhauer et al. | 562/414 |
| 4,910,175 | 3/1990 | Michel et al. | 502/24 |
| 4,933,491 | 6/1990 | Albertins et al. | 562/416 |
| 5,055,612 | 10/1991 | Tachibana et al. | 562/416 |

FOREIGN PATENT DOCUMENTS 1062279 9/1979 Canada .
0323309 7/1989 European Pat. Off. .

Primary Examiner—José G. Dees
Assistant Examiner—Vera C. Clarke
Attorney, Agent, or Firm—Thomas E. Nemo; Wallace L. Oliver; Frank J. Sroka

[57] ABSTRACT

Provided is a continuous process for producing 2,6-naphthalenedicarboxylic acid by the liquid phase oxidation of 2,6-dimethylnaphthalene comprising continuously adding to a reaction zone the oxidation reaction components comprising 2,6-dimethylnaphthalene, a source of molecular oxygen, a solvent comprising an aliphatic monocarboxylic acid, and a catalyst comprising cobalt, manganese and bromine components, wherein the atom ratio of manganese to cobalt is about 5:1 to about 0.3:1, the total of cobalt and manganese is at least about 0.40 weight percent based on the weight of solvent, and maintaining the contents of the reaction zone at a temperature of about 370° F. to about 420° F. and at a pressure sufficient to maintain at least a portion of the monocarboxylic acid in the liquid phase thereby oxidizing the 2,6-dimethylnaphthalene to 2,6-naphthalenedicarboxylic acid. By operating according to the process of this invention, 2,6-naphthalenedicarboxylic acid can be continuously produced in high yield and with low levels of impurities.

21 Claims, No Drawings

PROCESS FOR PREPARING 2,6-NAPHTHALENE-DICARBOXYLIC ACID

FIELD OF INVENTION

This invention relates to a process for the production of 2,6-naphthalenedicarboxylic acid by the liquid phase oxidation of 2,6-dimethylnaphthalene with a molecular oxygen-containing gas. More particularly, this invention relates to a continuous process for the production of 2,6-naphthalenedicarboxylic acid in high yield by the continuous liquid phase oxidation of 2,6-dimethylnaphthalene with a molecular oxygen-containing gas in the presence of a catalyst comprising heavy metal and bromine components.

BACKGROUND OF THE INVENTION 2,6-Naphthalenedicarboxylic acid (2,6-NDA) is a monomer useful for the preparation of high performance polymeric materials such as polyesters and polyamides. Polyethylene 2,6-naphthalate (PEN) is one such high performance polymer and it is prepared, for example, by the condensation of either 2,6-naphthalenedicarboxylic acid or dimethyl-2,6-naphthalenedicarboxylate with ethylene glycol. Fibers and films made from PEN have improved strength and thermal properties relative to, for example, fibers and films made from polyethylene terephthalate. High strength fibers made from PEN can be used to make tire cord, and films made from PEN are advantageously used to manufacture magnetic recording tape and electronic components. Also, because of its superior resistance to gas diffusion, and particularly to the diffusion of carbon dioxide, oxygen and water vapor, films made from PEN are useful for manufacturing food containers, particularly so-called "hot fill" type food containers.

In order to prepare high quality PEN suitable for the aforementioned applications, it is desirable to start with purified 2,6-naphthalenedicarboxylic acid or purified dimethyl-2,6-naphthalenedicarboxylate (DM-2,6-NDC). Since dimethyl-2,6-naphthalenedicarboxylate is typically prepared by the esterification of 2,6-naphthalenedicarboxylic acid using methanol, a purer form of 2,6-naphthalenedicarboxylic acid provides for purer dimethyl-2,6-naphthalenedicarboxylate. It is therefore advantageous to have the highest purity 2,6-naphthalenedicarboxylic acid.

2,6-Naphthalenedicarboxylic acid is most conveniently prepared by the liquid phase, heavy metal catalyzed oxidation of 2,6-dimethylnaphthalene using molecular oxygen, and particularly air, as the source of oxygen for the oxidation reaction. During this oxidation, the methyl substituents on the naphthalene ring of 2,6-dimethylnaphthalene are oxidized to carboxylic acid substituents. Processes for oxidizing 2,6-dimethylnaphthalene to 2,6-naphthalenedicarboxylic acid by such a liquid phase reaction are known. For example, U.S. Pat. No. 3,870,754 to Yamashita et al. discloses a process for oxidizing 2,6-dimethylnaphthalene in acetic acid solvent using molecular oxygen and a catalyst containing cobalt, manganese and bromine components, wherein the mole ratio of 2,6-dimethylnaphthalene to the acetic acid solvent is maintained at no greater than 1:100 and preferably no greater than 1:200.

U.S. Pat. No. 3,856,805 to Yamashita et al. discloses a process for oxidizing 2,6-dimethylnaphthalene in acetic acid using molecular oxygen and catalyzed by cobalt, manganese and bromine catalyst compounds at a reaction temperature no greater than 170° C. It is taught therein that oxidation temperatures exceeding 170° C. (338° F.) produce an extreme amount of by-products and coloration of the 2,6-naphthalenedicarboxylic acid. It is also taught that at temperatures exceeding 180° C., black "carbido-like" products are formed, and that it is impossible to obtain the intended naphthalenedicarboxylic acid in high yield. However, we have determined that low reaction temperatures do not provide for sufficiently reduced levels of 2-formyl-6-naphthoic acid. Additionally, lower reaction temperatures generally mean lower reaction rates, whereas rapid reaction rates are desirable for commercial processes.

During the liquid phase oxidation of 2,6-dimethylnaphthalene to 2,6-naphthalenedicarboxylic acid using a catalyst comprising cobalt, manganese and bromine components various side products are usually produced. For example, trimellitic acid (TMLA) is produced by the oxidation of one of the rings of the 2,6-dimethylnaphthalene molecule. 2-Formyl-6-naphthoic acid (FNA), a result of incomplete oxidation, is also produced. Bromination of the naphthalene ring during the oxidation reaction results in the formation of bromo naphthalenedicarboxylic acid (BrNDA). Additionally, loss of one methyl (or carboxylic acid) substituent during the oxidation reaction results in the formation of 2-naphthoic acid (2-NA). These side products, as well as a collection of other unidentified side products, are undesirable because, to some extent, they contaminate the 2,6-naphthalenedicarboxylic acid product, and their formation represents a reduced yield of the desired 2,6-naphthalenedicarboxylic acid. Additionally, trimellitic acid deactivates the oxidation catalysts by complexing to cobalt and manganese. Therefore, an oxidation process that produces trimellitic acid is self-deactivating. Finally, the contamination of the 2,6-naphthalenedicarboxylic acid by the side products produced during the oxidation reaction is a major problem because 2,6-naphthalenedicarboxylic acid, due to its high insolubility in ordinary solvents such as water, acetic acid, and aliphatic as well as aromatic hydrocarbons, is very difficult to purify by standard purification treatments such as recrystallization or adsorption. Therefore, it is important to produce 2,6-naphthalenedicarboxylic acid with low levels of these aforementioned impurities, and particularly trimellitic acid and 2-formyl-6-naphthoic acid.

The art needs a process for the continuous, liquid-phase oxidation of 2,6-dimethylnaphthalene suitable for large-scale commercial operations and that can produce 2,6-naphthalenedicarboxylic acid in high yield and having low levels of impurities such as trimellitic acid, 2-formyl-6-naphthoic acid, bromo naphthalenedicarboxylic acid as well as other impurities. The present invention provides such a process.

SUMMARY OF THE INVENTION

Provided is a process for producing 2,6-naphthalenedicarboxylic acid by the liquid phase oxidation of 2,6-dimethylnaphthalene, comprising: continuously adding to a reaction zone the oxidation reaction components comprising 2,6-dimethylnaphthalene, a source of molecular oxygen, a solvent comprising an aliphatic monocarboxylic acid, and a catalyst comprising cobalt, manganese and bromine components, wherein the weight ratio of monocarboxylic acid solvent to 2,6-dimethylnaphthalene is about 2:1 to about 12:1, the atom ratio of manganese to cobalt is about 5:1 to about 0.3:1, the atom ratio of bromine to the total of cobalt and manganese is about 0.3:1 to about 0.8:1, and the total of cobalt and manganese, calcualted as elemental cobalt and manganese, is at least about 0.40 weight percent based on the weight of solvent; maintaining the contents of the reaction zone at a temperature of about 370° F. to about 420° F. and at a pressure sufficient to maintain at least a portion of the monocarboxylic acid in the liquid phase thereby oxidizing the 2,6-dimethylnaphthalene to 2,6-naphthalenedicarboxylic acid; and continuously withdrawing from the reaction zone a product mixture comprising 2,6-naphthalenedicarboxylic acid. By operating according to the process of this invention 2,6-naphthalenedicarboxylic acid can be continuously produced in high yield and with low levels of impurities.

Additionally, the 2,6-naphthalenedicarboxylic acid produced by the process of this invention can be treated with a molecular oxygen-containing gas in order to reduce further the level of 2-formyl-6-naphthoic acid in the 2,6-naphthalenedicarboxylic acid and without appreciably changing the level of trimellitic acid. Furthermore, because the disclosed process requires a rather large amount of expensive catalyst metals, also provided is a means for recovering used oxidation catalyst metals which can then be returned to the oxidation reaction in a catalytically active state. This means for recovering the catalyst metals employs the direct recycle of a portion of the mother liquor obtained after the 2,6-naphthalenedicarboxylic acid is partitioned from the oxidation reactor product mixture, preferably in combination with the use of oxalic acid to precipitate and recover most of the valueable catalyst metals in the portion of the mother liquor that is not directly recycled to the oxidation reaction.

DETAILED DESCRIPTION OF THE INVENTION

The oxidation reaction in the process of this invention is a liquid phase reaction wherein a catalyst comprising cobalt, manganese and bromine components is used to catalyze the oxidation of the methyl substituents on 2,6-dimethylnaphthalene to carboxylic acid substituents. A gas containing molecular oxygen supplies the oxygen for the oxidation reaction, and water and carbon oxides are also produced. Importantly, the reaction is conducted in a continuous manner wherein the reaction components comprising the dimethylnaphthalene feedstock, the catalyst components, the source of molecular oxygen, and the solvent are continuously added to an oxidation reaction zone under predetermined reaction conditions and addition rates. Simultaneously, a reaction product mixture containing the desired 2,6-naphthalenedicarboxylic acid is removed from the reaction zone.

During the start up of the oxidation reaction, the composition of the reaction mixture in the oxidation reaction zone changes as the reaction proceeds. However, after a period of time, steady state conditions are achieved and the composition of the reaction mixture in the reaction zone becomes constant, i.e. so-called "lined-out" conditions are obtained. Due to its insolubility, the 2,6-naphthalenedicarboxylic acid product is typically in solid form and can be separated from the liquid part of the reaction product mixture, the so-called oxidation reaction mother liquor, by any suitable method for partitioning solids from liquids.

In greater detail, the hydrocarbon feedstock for the continuous oxidation process of this invention is 2,6-dimethylnaphthalene. This feedstock can be isolated from naphthalene-containing refinery streams including so-called tar fractions, or from one or more of the various "bottoms" produced during crude oil refining processes. However, the concentration of 2,6-dimethylnaphthalene in these refinery streams is generally low and, therefore, it is difficult to obtain suitably large quantities of the desired 2,6-dimethylnaphthalene feedstock. An alternate and presently preferable source of 2,6-dimethylnaphthalene is from one or more of the synthetic processes known for preparing 2,6-dimethylnaphthalene. One such route starts with o-xylene and butadiene wherein the o-xylene is alkenylated in the liquid phase with butadiene in the presence of an alkali metal catalyst such as sodium and/or potassium to form 5-ortho-tolyl pentene. Such an alkenylation reaction is disclosed in U.S. Pat. No. 3,953,535 to Shima et al. The 5-ortho-tolyl pentene is subsequently cyclized to form 1,5-dimethyltetralin, which is then dehydrogenated to form 1,5-dimethylnaphthalene. The 1,5-dimethylnaphthalene is isomerized to form 2,6-dimethylnaphthalene which can be isolated as a solid product. A suitable procedure for conducting these cyclization, dehydrogenation and isomerization reactions is disclosed in U.S. Pat. No. 4,950,825 to Sikkenga et al. Another process for preparing 2,6-dimethylnaphthalene starting from m-xylene, propylene and carbon monoxide is disclosed in U.S. Pat. No. 5,023,390 to Takafumi et al. However, any method or process for preparing or isolating 2,6-dimethylnaphthalene is suitable as a source of the 2,6-dimethylnaphthalene used in the process of this invention. Preferably, the 2,6-dimethylnaphthalene is at least about 98.5% and more preferably at least about 99% pure, by weight. We have determined that 2,6-dimethylnaphthalene isolated from refinery bottoms that is about 98.5% pure does not perform as well as 99% pure 2,6-dimethylnaphthalene in the oxidation process of this invention. Most preferably, therefore, the 2,6-dimethylnaphthalene should be at least 99% pure by weight. The purity of the 2,6-dimethylnaphthalene can conveniently be increased, for example, by a recrystallization process from a suitable solvent such as a low molecular weight alcohol having 1 to about 4 carbon atoms, and particularly methanol, or from a low molecular weight aliphatic carboxylic acid having 1 to about 4 carbon atoms. Acetic acid is a particularly preferred solvent for recrystallizing 2,6-dimethylnaphthalene because it is highly effective, relatively inexpensive and is also the solvent for the subsequent oxidation reaction. However, any method for increasing the purity of 2,6-dimethylnaphthalene, for example distillation, melt crystallization or adsorption is suitable.

The source of molecular oxygen employed in the liquid phase oxidation in the process of this invention can vary from pure oxygen to a gas containing about 0.1 percent by weight molecular oxygen, with the remaining gas being a ballast gas such as nitrogen that is inert in the liquid phase oxidation. Most preferably, for reasons of economy, the source of molecular oxygen is air. In order to avoid the formation of explosive mixtures, however, the molecular oxygen-containing gas that is introduced into the reaction zone should be added in an amount such that the exhaust gas mixture exiting the reaction zone contains from about 0.5 to 8 volume percent oxygen measured on a solvent-free basis.

The solvent for the liquid phase oxidation reaction comprises a low molecular weight aliphatic carboxylic acid having 1 to 6 carbon atoms, a mixture of two or more of such low molecular weight carboxylic acids, or a mixture of one or more of such low molecular weight carboxylic acids with water. Suitable solvents include, for example, acetic acid, propionic acid, n-butyric acid and mixtures of one or more of these acids with water. Preferably, due primarily to cost and availability, the oxidation solvent comprises acetic acid. Most preferably, the oxidation solvent comprises a mixture of acetic acid and water, wherein the water is suitably about 1 to about 20 weight percent, preferably about 1 to about 15 weight percent and most preferably about 1 to about 10 weight percent relative to the total of acetic acid and water added to the oxidation reaction zone. The weight ratio of aliphatic monocarboxylic acid solvent to 2,6-dimethylnaphthalene added to the oxidation reaction zone is in the range of about 2:1 to about 12:1, preferably in the range of about 3:1 to about 6:1, respectively. Low ratios of monocarboxylic acid solvent to 2,6-dimethylnaphthalene, i.e. 2:1 to 6:1 are advantageous because greater amounts of 2,6-naphthalenedicarboxylic acid can be produced per reactor volume. The ability to successfully oxidize 2,6-dimethylnaphthalene using low ratios of aliphatic monocarboxylic acid to 2,6-dimethylnaphthalene is one of the advantages of the process of this invention.

The oxidation reaction is an exothermic reaction and the heat that is generated is dissipated in part by the vaporization of the oxidation reaction solvent. Typically, a portion of the vaporized solvent is withdrawn from the reaction zone, cooled to condense the vapor, and the cooled liquid is returned to the oxidation reaction mixture. This vapor is typically a mixture of water and, when acetic acid is used as the aliphatic monocarboxylic acid solvent, acetic acid. By separating the water from the acetic acid before it is returned to the reaction zone, the water level in the reaction zone can, to a degree, be adjusted to levels lower than that which would otherwise develop in the reaction zone due to the formation of water during the oxidation reaction. The carbon oxides produced as a consequence of the oxidation reaction are vented from the reaction zone.

The catalyst employed in the liquid phase oxidation according to the process of this invention comprises cobalt, manganese and bromine components. Each of the cobalt and manganese components can be provided in any of its known ionic or combined forms that provides for soluble forms of cobalt and manganese in the oxidation reaction solvent. For example, one or more of cobalt and/or manganese acetate tetrahydrate, carbonate or bromide can be employed. The bromine component of the oxidation catalyst is provided by a suitable source of bromine which includes, for example, elemental bromine, i.e. $Br_2$, ionic bromide such as HBr, NaBr, KBr, $NH_4Br$, etc., or organic bromides which are known to provide bromide ions at the operating temperature of the oxidation such as, for example, benzylbromide, mono- and dibromoacetic acid, bromoacetyl bromide, tetrabromoethane, ethylene dibromide, etc.

We have determined that in order to obtain a reaction product containing suitably low levels of trimellitic acid and other reaction side products in the continuous oxidation process of this invention, it is necessary to add the cobalt and manganese oxidation catalyst components to the reaction zone in an amount such that the total of cobalt and manganese, calculated as elemental cobalt and manganese, is at least about 0.40 weight percent, preferably at least about 0.50 weight percent, and most preferably, at least about 0.70 weight percent based on the weight of the aliphatic monocarboxylic acid oxidation solvent added to the reaction zone. Although catalyst metal levels above 1.2 weight percent based on the weight of the solvent can be used, it is generally preferable, primarily for economic reasons, to maintain the level of catalyst metals below about 1.2 and more preferably, below about 1.0 weight percent based on the weight of the aliphatic monocarboxylic acid solvent added to the reaction zone.

The atom ratio of manganese to cobalt in the oxidation catalyst is about 5:1 to about 0.3:1, preferably about 4:1 to about 0.5:1 and most preferably about 4:1 to about 2.5:1. Manganese is less expensive than cobalt, therefore, it is advantageous to use as much manganese as possible. Additionally, we have determined that high atom ratios of manganese to cobalt, i.e. atom ratios of greater than about 2.5:1 in the continuous oxidation process of this invention, provide for lower amounts of trimellitic acid relative to manganese to cobalt atom ratios of about 1:1. This, therefore, is another reason to use atom ratios of manganese to cobalt of greater than about 2:1, and preferably greater than about 2.5:1. As used herein, "atom ratio" is the atomic ratio of catalyst components, for example, the ratio of milligram atoms of elemental manganese to milligram atoms of elemental cobalt, or, as discussed below, the milligram atoms of bromine measured as atomic bromine to the total of the milligram atoms of cobalt and the milligram atoms of manganese.

The atom ratio of the bromine component in the catalyst for the oxidation process of this invention to the total of the cobalt and manganese components, is in the range of about 0.3:1 to about 0.8:1, and preferably about 0.4:1 to about 0.7:1. Atom ratios of bromine to the total of cobalt and manganese of less than about 0.3:1 can produce colored product. If the atom ratio of bromine to the total of cobalt and manganese exceeds 0.8:1, a large amount of brominated products such as bromo naphthalenedicarboxylic acid will be formed. The individual catalyst components can be introduced into the reaction zone where the liquid phase oxidation is occurring either separately or in one or more combinations, and they can be introduced in any convenient manner, for example, as a solution in water or a mixture of water and the monocarboxylic acid oxidation solvent, or other suitable solvent.

The reaction temperature for the liquid phase oxidation according to the process of this invention is in the range of about 370° F. to about 420° F., and preferably in the range of about 380° F. to about 415° F. Reaction temperatures higher than about 420° F. or lower than about 370° F. cause reduced yields of the desired 2,6-naphthalenedicarboxylic acid. Also, at oxidation reaction temperatures above about 420° F., excessive amounts of trimellitic acid are formed, and at oxidation reaction temperatures below about 370° F., the level of 2-formyl-6-naphthoic acid increases. Additionally, oxidation at temperatures below about 370° F. decreases the rate of the oxidation reaction and it is therefore preferable, particularly for large scale commercial operations, to conduct the liquid phase oxidation reactions at as high a temperature as possible without causing the production of excessive amounts of undesirable reaction side products that contaminate the 2,6-naphthalenedicarboxylic acid and make it more difficult to purify.

The apparatus used to conduct the oxidation reaction can be a tank reactor (preferably stirred), a plug flow reactor, a compartmented reactor such as that disclosed in Holzhauer et al. U.S. patent application Ser. No. 561,063, filed on Aug. 1, 1990, or a combination of two or more of these reactors. For example, the apparatus can consist of two or three stirred tank reactors arranged in series. Optionally, a plug flow reactor can suitably be used to mix and pre-heat the reactants before they enter the stirred tank reactor or reactors.

In operation, the minimum pressure at which the oxidation reaction is maintained is preferably a pressure which will maintain at least 50 weight percent and more preferably at least 70 weight percent of the solvent in the reaction zone in the liquid phase. When the solvent is a mixture of acetic acid and water, suitable reaction pressures are from about 0.1 atmosphere absolute to about 35 atmospheres absolute, and typically in the range of about 10 atmospheres absolute to about 30 atmospheres absolute.

During the oxidation reaction of this invention, 2,6-dimethylnaphthalene can be added to the oxidation reaction zone at various rates. The rate at which the 2,6-dimethylnaphthalene is added is related to the solvent ratio and the reactor residence time. The solvent ratio is the amount, by weight, of solvent added to the reaction zone divided by the amount, by weight, of 2,6-dimethylnaphthalene added to the oxidation reaction zone. The reactor residence time in minutes is the oxidation reactor drain weight in pounds divided by the reaction mixture effluent rate in pounds per minute. The solvent ratio and residence time are related to a value termed "hydrocarbon throughput" or HCTP. HCTP, as used herein, is pound moles of 2,6-dimethylnaphthalene added per cubic foot of reaction solvent in the reactor per hour, and is a measure of productivity for the oxidation reactor. HCTP is suitably in the range of about 0.02 to about 0.20, preferably about 0.04 to about 0.16, and most preferably about 0.06 to about 0.16. When it is desirable to operate at low HCTP values, i.e. about 0.02 to about 0.08, the continuous oxidation reaction of this invention can be conducted using a lower amount of cobalt and manganese catalyst metals, i.e. a total of cobalt and manganese, calculated as elemental cobalt and manganese, in the range of about 0.40 to about 0.70 weight percent based on the aliphatic monocarboxylic acid oxidation solvent. HCTP values in the range of about 0.02 to about 0.08 provides for decreased formation of trimellitic acid when catalyst levels at the low end of the hereinabove disclosed range are used. Conversely, when it is desirable to operate at high HCTP values, i.e. about 0.06 to about 0.20, higher levels of catalyst are required wherein the total of cobalt and manganese, calculated as elemental cobalt and elemental manganese, is greater than about 0.60 weight percent based on the weight of the aliphatic monocarboxylic acid oxidation solvent. High HCTP values are desirable for achieving maximum production rates for a fixed sized manufacturing plant. The use of lower HCTP values is advantageous when the production of a manufacturing plant needs to be reduced to compensate for changing demand.

The oxidation reaction mixture produced in the reaction zone during the liquid phase oxidation reaction is continuously removed from the reaction zone typically in the form of a slurry of solid 2,6-naphthalenedicarboxylic acid in the reaction mixture mother liquor. The mother liquor typically comprises the low molecular weight monocarboxylic acid solvent, water, dissolved impurities and catalyst components. The desired 2,6-naphthalenedicarboxylic acid is separated from the mother liquor by one or more suitable methods for partitioning a solid from a liquid phase such as, for example, centrifugation, filtration, settling, etc. However, prior to this partitioning step, the oxidation reaction mixture can be cooled. The cooling can be accomplished by any convenient method, for example, a tube and shell-type heat exchanger can be used, or the reaction mixture can be cooled in a vessel equipped with cooling coils or a cooled reactor jacket. Alternatively, the reaction mixture can be added to a vessel at a pressure lower than that used for the oxidation reaction. At the reduced pressure the oxidation reaction solvent boils thereby cooling the reaction mixture. An overhead condenser can be used to cool, condense and return the overhead vapor to the vessel to further assist in the cooling. Two or more of these vessels can be used in series, each at a temperature somewhat lower than the previous vessel, to cool the reaction mixture in a stagewise manner. The oxidation reaction mixture is typically cooled to about 250° F. or below prior to partitioning the 2,6-naphthalenedicarboxylic acid from the oxidation reaction mother liquor.

After the oxidation reaction mixture exits the oxidation reaction zone, but prior to the partitioning of the 2,6-naphthalenedicarboxylic acid from the mother liquor, it is also desirable to again contact the reaction product mixture with an oxygen containing gas in the absence of freshly added 2,6-dimethylnaphthalene. We have determined that such a treatment provides for a substantial and desirable reduction of the level of 2-formyl-6-naphthoic acid in the reaction mixture and, unexpectedly, does not significantly increase the level of trimellitic acid in the reaction mixture.

This treatment of the oxidation reaction mixture with a molecular oxygen-containing gas in the absence of freshly added 2,6-dimethylnaphthalene can be conducted at any time after the reaction mixture exits the oxidation reaction zone, and it can be conducted in any suitable manner whereby the molecular oxygen-containing gas is contacted with the reaction mixture at an elevated temperature and preferably at a temperature in the range of about 150° F. to about 450° F. Most preferably, however, the reaction mixture, as it exits the oxidation reaction zone, is directly contacted with an oxygen-containing gas in one or more suitable reactor vessels such as a tank reactor or a compartmented reactor. Advantageously, a tank reactor is used, with or without an agitator, and the molecular oxygen-containing gas is sparged into the reactor, preferably at a point at the bottom of the reactor. The temperature is suitably in the range of about 350° F. to about 450° F. Although the rate of introduction of oxygen-containing gas is not critical, there should be sufficient molecular oxygen present to oxidize the formyl groups within a residence time of about 0.25 hour to about 2 hours at the temperature used. As with the continuous oxidation, the vent gas composition must be controlled to prevent the formation of explosive mixtures. It is also possible to treat the reaction mixture with the oxygen-containing gas when the oxidation reaction mixture is being cooled, as described above. Thus, for example, while the reaction mixture is held at reduced pressure to provide for the cooling of the reaction mixture, the oxygen-containing gas is sparged through the reaction mixture. The oxygen-containing gas can contain from about 0.1 weight percent molecular oxygen to pure oxygen, with the remaining gas being an inert ballast gas such as nitrogen.

In a similar procedure, the 2,6-naphthalenedicarboxylic acid, after being separated from the reaction mixture mother liquor, can be redispersed or suspended in a suitable solvent such as water, a low molecular weight carboxylic acid or a mixture of water and a low molecular weight carboxylic acid at a weight ratio of about 0.1 to about 25 parts of 2,6-naphthalenedicarboxylic acid per part of solvent. This dispersion or suspension can then be heated to a temperature in the range of 200° F. to about 450° F. and sparged with a molecular oxygen-containing gas for a time sufficient to reduce the level of 2-formyl-6-naphthoic acid contained therein.

The mother liquor that is separated from the oxidation reaction mixture contains most of the oxidation metal catalyst components and, typically, most of the water that may have been added to the reaction mixture as well as the water produced during the oxidation reaction. However, the mother liquor also contains undesirable reaction side products such as trimellitic acid. Nevertheless, this mother liquor is valuable because it can be recycled to the oxidation reaction zone as a source of acetic acid and, more importantly, as a source of active catalyst metals. The mother liquor can be recycled to the oxidation reacting zone in an amount in the range of about 1 weight percent of the mother liquor to about 100 weight percent. Preferably, about 5 to about 50 weight percent of the mother liquor is recycled, the remaining portion typically being treated to recover the acetic acid. We have determined, however, that it is preferable to recycle an amount of the mother liquor to the reaction zone so that the ratio of gram moles of trimellitic acid present in the reaction mixture to the total gram atoms of cobalt and manganese present in the reaction mixture does not exceed about 1.0, preferably does not exceed about 0.70, and most preferably does not exceed about 0.5. Furthermore, it is advantageous to maintain the amount of water in the reaction zone to a level that is no more than about 15, preferably no more than about 12, and most preferably, no more than about 10 weight percent of the oxidation solvent. When the amount of trimellitic acid and/or water exceeds these limits because of recycle there is an increase in the production of reaction side products such as bromo naphthalenedicarboxylic acid and trimellitic acid.

In one embodiment of the present invention water is added to the effluent from the oxidation reaction zone either before or after the optional treatment with an oxygen-containing gas in order to increase the solubility of the oxidation catalyst metals, trimellitic acid, and the products that are formed by the complexation of trimellitic acid with the cobalt and manganese oxidation catalyst metals. The addition of water decreases the amount of metals and trimellitic acid that would otherwise be incorporated in the 2,6-naphthalenedicarboxylic acid when it is partitioned from the mother liquor. The amount of water added to the oxidation reactor effluent is an amount that provides for a mother liquor that is not more than about 50 weight percent and preferably not more than about 30 weight percent water. However, when this amount of water is added to the oxidation reaction effluent, the amount of mother liquor recycled to the oxidation reaction generally has to be reduced in order to prevent an excessive amount of water in the oxidation reaction. As stated above, the levels of the bromo naphthalenedicarboxylic acid and trimellitic acid are increased in the oxidation reaction product if the level of water in the oxidation reaction exceeds about 15 weight percent of the total oxidation reaction solvent. Therefore, if water is added to the effluent from the oxidation reaction zone in order to solubilize the oxidation catalyst metals and trimellitic acid, the amount of mother liquor recycled to the reactor must be limited so that the amount of water in the oxidation reaction mixture is within the hereinabove described levels. Otherwise, water must be removed from the mother liquor before it is added to the oxidation reaction mixture, or water must be removed from the oxidation reaction mixture during the oxidation. One method for removing water from the mother liquor comprises thermally dehydrating the mother liquor. Another method comprises treating the mother liquor with an agent to adsorb or react with water and, thereby, eliminating water from the mother liquor. For example, a molecular sieve adsorbent can be used to remove water or a carboxylic acid anhydride, such as acetic anhydride, can be added to remove the water.

A convenient method for removing water from the oxidation reaction mixture during the oxidation reaction comprises removing a vaporous mixture of monocarboxylic acid reaction solvent and water produced during the exothermic oxidation reaction and returning to the oxidation reaction mixture aliphatic monocarboxylic acid solvent containing less water than that removed as a vapor. For example, the vaporous mixture can be condensed and the condensate treated to separate the water from the monocarboxylic acid solvent. The monocarboxylic acid solvent free of most or all of the water is then returned to the oxidation reaction. This operation suitably provides for the removal of water from the oxidation reaction mixture and allows for the direct recycle of greater quantities of mother liquor-containing water.

We have also determined that a preferred method for recycling the valuable catalyst metals to the oxidation reaction zone comprises precipitating the catalyst metals with oxalic acid to form the oxalic acid complex of the catalyst metals. Oxalic acid complexes have only a low solubility in the mother liquor. Consequently, after adding the oxalic acid to the mother liquor, the oxalic acid complexes precipitate from the mother liquor and can be collected using one or more methods for partitioning solids from a liquid phase, e.g. centrifugation, filtration, etc. These oxalic acid complexes can be added directly to the oxidation reaction mixture. Optionally, the recovered oxalic acid complexes of cobalt and manganese can be heated to a temperature sufficient to decompose the complexes thereby converting them to a form that is soluble in acetic acid. One such method comprises heating the oxalic acid complexes, optionally in acetic acid, at a temperature greater than about 500° F., preferably in the presence of HBr, and preferably for about 0.25 hour to about 2 hours.

The reaction of the oxidation reaction mother liquor with oxalic acid to precipitate the oxalic acid complexes of cobalt and manganese is conveniently accomplished by heating the mother liquor with oxalic acid, preferably at a temperature in the range of about 100° F. to about 240° F. The ratio of oxalic acid to the total of cobalt and manganese in the mother liquor is suitably in the range of about 0.6 to about 3.0 gram mole of oxalic per gram atom of total cobalt and manganese in the mother liquor, although more or less oxalic acid can be used. Significantly, when oxalic acid is used to remove the valuable catalyst metals from the mother liquor, most of the water, trimellitic acid, and bromine remain with the mother liquor in the filtrate. The filtrate can be treated to remove the acetic acid by one or more suitable methods such as distillation and the acetic acid recycled. Additionally, during the process wherein the oxalate complexes of cobalt and manganese are separated from the mother liquor, additional 2,6-naphthalenedicarboxylic acid is recovered. This 2,6-naphthalenedicarboxylic acid exists as "fines" in the mother liquor that typically passes through the apparatus used to partition the 2,6-naphthalenedicarboxylic acid from the mother liquor. It is to be understood that the use of oxalic acid in the method disclosed herein incorporates any convenient source of oxalic acid, including salts such as sodium or potassium or ammonium oxalate, aqueous solutions of oxalic acid or any other compound that effectively provides for oxalate, i.e. $C_2O_4=$.

The use of the oxalate salts to recover cobalt and manganese for recycle can be used either exclusively, or, preferably, in combination with the recycle of untreated mother liquor. For example, about 5 to about 50 percent, preferably 10 to about 30 percent of the mother liquor can be directly recycled to the oxidation reactor and the remaining portion of the mother liquor treated with oxalic acid to recover the cobalt and manganese as the oxalate complexes, which are then at least in part recycled to the oxidation reaction mixture. This method of directly recycling a portion of the mother liquor and recycling the catalyst metals in the remaining portion of the mother liquor as their oxalic acid complexes is highly advantageous. As described above, only a certain proportion of the mother liquor can be directly recycled before the contaminants in the mother liquor, e.g. trimellitic acid, cause adverse effects. However, the use of oxalic acid or other source of oxalate to precipitate the cobalt and manganese from the mother liquor provides for the separation of the valuable catalyst metals from the impurities in the mother liquor. Consequently, it is advantageous, primarily for economic reasons, to directly recycle as much of the mother liquor to the oxidation reaction as possible without adversely affecting the oxidation reaction, and then recover the catalyst metals in the remaining mother liquor as the oxalic acid complexes and recycling these recovered catalyst metals to the oxidation reaction.

Although the hereinabove described processes for returning oxidation catalyst metals and oxidation reaction solvent to the oxidation reaction mixture are described with respect to a continuous-mode oxidation reaction, it is to be understood that these processes for reusing oxidation catalyst metals and solvent also apply to an oxidation reaction of 2,6-dimethylnaphthalene conducted in either the semi-continuous or batch manner. By semi-continuous it is meant that at least one of the reaction components, but less than all, is added to the oxidation reaction zone during the course of the oxidation. For example, a suitable reactor is charged with oxidation solvent, catalyst metals and a source of bromine. The 2,6-dimethylnaphthalene is gradually added to the reaction vessel while simultaneously adding molecular oxygen. In a batch mode operation, all of the reaction components are added initially and the molecular oxygen is added during the reaction since it is difficult, and hazardous, to add all of the oxygen required to complete the oxidation reaction of 2,6-dimethylnaphthalene to 2,6-naphthalenedicarboxylic acid at once.

The present invention will be more clearly understood from the following examples. It being understood, however, that these examples are presented only to illustrate embodiments of the present invention and are not intended to limit the scope thereof.

EXAMPLES

The continuous oxidation reactions described in Examples 1 through 7 below were conducted in a five gallon stirred titanium pressure reactor equipped with an overhead condenser and lines for adding the reaction components and removing the product mixture. The reactor was maintained at approximately the 50% full level. The 2,6-dimethylnaphthalene oxidation feedstock material was maintained at about 225° F. to keep it in the liquid state, and it was added to the reactor using a piston-type pump. Solvent (acetic acid) and the catalyst components (as a solution in aqueous acetic acid) were separately pumped into the reactor also using piston-type pumps. The oxidation solvent added to the reactor was typically about 95 weight percent acetic acid and 5 weight percent water. Compressed air was added at a rate to achieve about 4-6% oxygen in the reactor vent gas stream. The reaction solvent containing acetic acid and water was condensed in the overhead condenser and returned to the reactor. In order to be certain that so-called "lined out" conditions were achieved, i.e. where the composition of the reactor achieved a steady state composition, the continuous oxidation reaction reported in Examples 1 through 7 below were permitted to proceed for about four reactor residence times before a sample was taken for analysis. The organic reaction products were analyzed using liquid chromatography. Catalyst metal and bromine concentrations were measured by x-ray fluorescence spectroscopy. A slip-stream from the reactor off-gas was also continuously analyzed to determine off-gas oxygen, carbon monoxide and carbon dioxide levels. The fresh cobalt and manganese catalyst components were added as their hydrated acetate salts, i.e. Co $(OAc)_2.4H_2O$ and Mn $(OAc)_2.4H_2O$. Bromine was added as an aqueous solution of hydrogen bromide.

In the following Examples, "TMLA" is trimellitic acid, "2,6-NDA" is 2,6-naphthalenedicarboxylic acid, "Br-NDA" is bromo-2,6-naphthalenedicarboxylic acid, "FNA" is 2-formyl-6-naphthoic acid and "2-NA" is 2-naphthoic acid. "Reactor Yield" or "Molar Reactor Yield," is the percent yield of each component listed in the oxidation reactor effluent and based on the moles of the component produced relative to the moles of 2,6-dimethylnaphthalene feedstock added. The values reported for carbon monoxide and carbon dioxide are the amounts of those oxidation products produced in gram moles per hour. "HCTP" corresponds to hydrocarbon throughput and is defined as the molar feed rate of 2,6-dimethylnaphthalene in pound moles per hour divided by the volume of solvent in the oxidation reactor. The units for HCTP are pound moles of 2,6-dimethylnaphthalene added to the reactor per cubic foot of reactor solvent in the reactor, per hour. "Solvent Ratio" is approximately the rate of removal of solvent by weight divided by the rate of addition of 2,6-dimethylnaphthalene by weight. This value approximately equals the rate of addition of oxidation reaction solvent divided by the rate of addition of 2,6-dimethylnaphthalene, by weight, i.e. the amount of solvent exiting the oxidation reactor may be greater than that added due to the formation of water in the reaction by the oxidation reaction. "Residence Time" is the oxidation reactor drain weight divided by the reaction mixture effluent rate in pounds per minute. "Wt. % Co" is the weight percent cobalt, measured as elemental cobalt, based on the oxidation reaction solvent added to the oxidation reactor. "Co:Mn:Br." is the gram atom ratio of cobalt:manganese:bromine in the catalyst added to the oxidation reaction mixture. The molten 2,6-dimethylnaphthalene (DMN) feed rate values are in pounds per hour.

EXAMPLE 1

Table I lists the results for the continuous oxidation of 2,6-dimethylnaphthalene (feedstock) under similar oxidation conditions using a high purity (99+%) feedstock and a 98.5% pure feedstock. The 2,6-dimethylnaphthalene was obtained from oil refinery bottom streams. The 99+% purity material was obtained from the 98.5% purity 2,6-dimethylnaphthalene by two recrystallizations from acetic acid.

These data show that the yield of 2,6-naphthalenedicarboxylic acid is greater using the purer feedstock. Less reaction impurities such as Br-NDA, FNA and 2-NA are also formed from the oxidation of the purer feedstock.

EXAMPLE 2

Table II lists the results from a series of continuous oxidation runs conducted at reaction temperatures ranging from 380° F. to 420° F. These data demonstrate that as the reaction temperature is reduced from about 400° F., the level of FNA begins to increase in the reaction effluent. Conversely, as the reaction temperature is increased, the yield of 2,6-naphthalenedicarboxylic acid decreases and the level of TMLA increases.

TABLE I

|  | Run 1 | Run 2 |
|---|---|---|
| Conditions |  |  |
| Feedstock Purity, wt. % | 98.5 | 99+ |
| Wt. % Co | 0.15 | 0.15 |
| Co:Mn:Br | 1.0:3.0:2.0 | 1.0:3.0:2.0 |
| Reaction Temp., °F. | 380 | 385 |
| Solvent Ratio, by weight | 6:1 | 6:1 |
| Reactor Residence Time (min) | 80 | 90 |
| Molar Reactor Yields |  |  |
| TMLA | 3.70 | 2.56 |
| 2,6-NDA | 81.98 | 93.35 |
| Br-NDA | 1.43 | 0.51 |
| FNA | 1.80 | 0.44 |
| 2-NA | 0.24 | 0.27 |

TABLE II

|  | Run 3 | Run 4 | Run 5 | Run 6 | Run 7 |
|---|---|---|---|---|---|
| Conditions |  |  |  |  |  |
| Reaction Temp. °F. | 380 | 400 | 408 | 415 | 420 |
| Reaction Press., PSIG | 215.2 | 283.1 | 307.7 | 345.8 | 361.0 |
| Wt. % Co | 0.19 | 0.19 | 0.19 | 0.19 | 0.19 |
| Co:Mn:Br | 1:3:2 | 1:3:2 | 1:3:2 | 1:3:2 | 1:3:2 |
| DMN Feed Rate | 4.2 | 4.2 | 5.1 | 4.2 | 5.1 |
| Solvent Ratio | 4.1 | 4.0 | 3.9 | 4.0 | 3.4 |
| HCTP | 0.12 | 0.12 | 0.12 | 0.12 | 0.13 |
| $CO_2$ g moles/hr | 3.61 | 6.83 | 7.43 | 9.61 | 9.89 |
| CO$_2$ g moles/hr | 0.95 | 1.92 | 2.51 | 2.89 | 3.30 |
| Total CO & $CO_2$ | 4.56 | 8.75 | 9.94 | 12.50 | 13.19 |
| Reactor Yields |  |  |  |  |  |
| TMLA | 2.85 | 2.75 | 3.42 | 2.97 | 3.65 |
| 2,6-NDA | 93.22 | 91.95 | 92.41 | 93.65 | 85.90 |
| FNA | 1.28 | 0.62 | 0.53 | 0.39 | 0.29 |

TABLE II-continued

|  | Run 3 | Run 4 | Run 5 | Run 6 | Run 7 |
|---|---|---|---|---|---|
| 2-NA | 0.12 | 0.18 | 0.27 | 0.22 | 0.26 |

EXAMPLE 3

Table III lists the results from a series of continuous oxidation runs conducted under substantially similar conditions except that the composition of cobalt, manganese and bromine oxidation catalyst was varied. A comparison of the results from runs 8, 9 and 10 demonstrate that at reduced ratios of manganese to cobalt in the catalyst there is an increase in the production of trimellitic acid (TMLA) from about 2.1% at a 3:1 manganese to cobalt ratio, to about 3.1% at a manganese to cobalt ratio of about 1:1. Although the amount of Br-NDA in the product was greater when the higher ratio of manganese to cobalt was used in Run 10, the yield of Br-NDA is still however relatively low at 0.44%. The elevated amount of Br-NDA produced in Run 10 is likely due, at least in part, to the higher levels of bromine relative to the amounts used in Runs 8 and 9. Atom ratios of bromine to cobalt plus manganese above about 0.8 are, therefore, expected to produce greater amounts of Br-NDA.

EXAMPLE 4

Table IV lists the results from a series of continuous oxidation runs conducted under substantially similar conditions as those for Runs 4, 6 and 7 reported in Table II except that the weight percent of cobalt and, therefore, the total level of catalyst metals, was lower for Runs 11, 12 and 13 reported in Table IV than for the Runs 4, 6 and 7. These data clearly demonstrate that higher yields of the desired 2,6-naphthalenedicarboxylic acid are obtained using the higher level of catalyst metals, and the amount of TMLA produced is lower using the higher levels of catalyst metals.

TABLE III

|  | Run 8 | Run 9 | Run 10 |
|---|---|---|---|
| Conditions |  |  |  |
| Wt. % Co | 0.30 | 0.225 | 0.15 |
| Co:Mn:Br | 1:1:0.5 | 1:1:0.6 | 1:3:2 |
| Reaction Temp., °F. | 385 | 385 | 385 |
| Solvent Ratio | 5.9 | 6 | 6.1:1 |
| Residence Time (min) | 90 | 90 | 90 |
| HCTP | 0.039 | 0.039 | 0.037 |
| Reactor Yields |  |  |  |
| TMLA | 3.10 | 3.11 | 2.14 |
| 2,6-NDA | 93.21 | 92.79 | 92.02 |
| Br-NDA | 0.12 | 0.07 | 0.44 |
| FNA | 0.38 | 0.39 | 0.53 |
| 2-NA | 0.28 | 0.31 | 0.21 |

TABLE IV

|  | Run 11 | Run 12 | Run 13 |
|---|---|---|---|
| Conditions |  |  |  |
| Reaction Temp., °F. | 400 | 414 | 420 |
| Reaction Press., PSIG | 274.2 | 340.3 | 354.1 |
| Wt. % Co | 0.15 | 0.15 | 0.15 |
| Co:Mn:Br | 1:3:2 | 1:3:2 | 1:3:2 |
| DMN Feed Rate | 5.1 | 5.1 | 5.6 |
| Solvent Ratio | 4.0 | 4.3 | 4.1 |
| HCTP | 0.13 | 0.12 | 0.14 |
| $CO_2$ g moles/hr | 6.82 | 7.99 | 9.20 |
| CO g moles/hr | 1.56 | 2.16 | 1.86 |
| Total CO & $CO_2$ | 8.38 | 10.15 | 11.06 |
| Reactor Yields |  |  |  |

TABLE IV-continued

|  | Run 11 | Run 12 | Run 13 |
|---|---|---|---|
| TMLA | 8.63 | 5.08 | 11.77 |
| 2,6-NDA | 82.97 | 85.23 | 77.06 |
| FNA | 1.19 | 0.33 | 1.66 |
| 2-NA | 2.42 | 0.25 | 0.59 |

EXAMPLE 5

Table V lists the results from a series of continuous oxidation runs conducted at substantially similar conditions except that the hydrocarbon throughput (HCTP) was varied. In these examples the HCTP was varied by varying the rate of addition of the molten DMN feedstock. As the data demonstrates, the yield increases and, importantly, the amount of trimellitic acid produced decreases as the HCTP is decreased.

TABLE V

|  | Run 14 | Run 15 | Run 16 |
|---|---|---|---|
| Conditions |  |  |  |
| Reaction Temp., °F. | 415 | 414 | 415 |
| Reaction Press., PSIG | 346.1 | 340.3 | 336.9 |
| Wt. % Co | 0.15 | 0.15 | 0.15 |
| Co:Mn:Br | 1:3:2 | 1:3:2 | 1:3:2 |
| DMN Feed Rate | 3.0 | 5.1 | 6.0 |
| Solvent Ratio | 4.0 | 4.3 | 4.2 |
| HCTP | 0.07 | 0.12 | 0.16 |
| $CO_2$ g moles/hr | 7.41 | 7.99 | 9.75 |
| CO g moles/hr | 2.39 | 2.16 | 2.85 |
| Total CO & $CO_2$ | 9.80 | 10.15 | 12.60 |
| Reactor Yields |  |  |  |
| TMLA | 4.58 | 5.08 | 5.33 |
| 2,6-NDA | 90.39 | 85.23 | 89.50 |
| FNA | 0.22 | 0.33 | 0.40 |
| 2-NA | 0.51 | 0.25 | 0.31 |

Therefore, the increase in the amount of trimellitic acid formed by using lower catalyst concentrations, can, in part, be offset by using lower HCTP. However, lower HCTP requires a lower production rate for 2,6-naphthalenedicarboxylic acid and, therefore, a compromise between catalyst concentration and HCTP must be made.

EXAMPLE 6

Table VI lists the results of a series of continuous oxidation reactions where the effluent from the oxidation reator was immediately directed to a second, equally-sized vessel and treated with a mixture of 5-8% (by volume) molecular oxygen in nitrogen gas at a rate of about 10-12 standard cubic feet per hour at the temperatures indicated.

As shown by the data under the heading "Reactor Yield Following Oxygen Treatment," treating the reactor effluent with molecular oxygen substantially reduced the level of 2-formyl-6-naphthoic acid 18 to 38.5 percent without substantially changing the amount of trimellitic acid in the product.

Table VII compares the results from an average of eight continuous oxidation reactions and the data in this table demonstrates that by treating the oxidation reactor product with molecular oxygen (5-8% by volume in nitrogen) after the product exits the oxidation reactor reduces the amount of 2-formyl-6-naphthoic acid present approximately 35 percent without substantially increasing the amount of trimellitic acid in the product.

EXAMPLE 7

A continuous oxidation of 2,6-dimethylnaphthalene was carried out in a manner similar to that used in preceding Examples 1-6 except that most of the catalyst used for the oxidation was from the mother liquor recovered from a previous, similarly conducted continuous oxidation of 2,6-dimethylnaphthalene. The recycled mother liquor supplied 77 weight percent of the cobalt, 41 weight percent of manganese and 53 weight percent of the bromine. The remaining catalyst components were supplied as fresh components. The results from this continuous oxidation are reported in Table VIII. By using the mother liquor from a previous continuous oxidation reaction as part of the solvent and as a source of metals for a second continuous oxidation reaction, the level of impurities in the second oxidation-impurities that could affect the course of the oxidation reaction-is approximately the same as that in a continuous oxidation under steady state conditions where 50 percent recycle is used. Thus, the use of the mother liquor from a previous oxidation reaction as the solvent for a new oxidation reaction simulates continuous 50 percent mother liquor recycle.

The data in Table VIII establishes that this level of recycle does not substantially affect the continuous oxidation reaction.

TABLE VI

|  | Run 17 | Run 4 | Run 3 | Run 6 |
|---|---|---|---|---|
| Conditions |  |  |  |  |
| Reaction Temp., °F. | 400 | 400 | 380 | 415 |
| Reaction Press., PSIG | 283.1 | 283.1 | 215.2 | 345.8 |
| Wt. % Co | 0.19 | 0.19 | 0.19 | 0.19 |
| Co:Mn:Br | 1:3:2 | 1:3:2 | 1:3:2 | 1:3:2 |
| DMN Feed Rate | 4.2 | 4.2 | 4.2 | 4.2 |
| Solvent Ratio | 4.0 | 4.0 | 4.1 | 4.0 |
| HCTP | 0.12 | 0.12 | 0.12 | 0.12 |
| $CO_2$ g moles/hr | 6.75 | 6.83 | 3.61 | 9.61 |
| CO g moles/hr | 2.15 | 1.92 | 0.95 | 2.89 |
| Total CO & $CO_2$ | 8.90 | 8.75 | 4.56 | 12.50 |
| Reactor Yield |  |  |  |  |
| TMLA | 2.59 | 2.75 | 2.85 | 2.97 |
| 2,6-NDA | 90.59 | 91.95 | 93.22 | 93.65 |
| FNA | 0.59 | 0.62 | 1.28 | 0.39 |
| 2-NA | 0.15 | 0.18 | 0.12 | 0.22 |
| Subsequent Oxygen Treatment, Conditions |  |  |  |  |
| Temperature, °F. | 345 | 370 | 350 | 377 |
| Gas Rate, SCFH | 10.4 | 12.0 | 10.3 | 12.0 |
| Reactor Yield Following Oxygen Treatment |  |  |  |  |
| TMLA | 2.70 | 2.63 | 2.91 | 3.07 |
| 2,6-NDA | 93.40 | 89.02 | 94.40 | 94.87 |
| FNA | 0.47 | 0.41 | 1.05 | 0.24 |
| 2-NA | 0.19 | 0.17 | 0.12 | 0.24 |
| % Change in FNA | −20.3 | −33.9 | −18.0 | −38.5 |
| % Change in TMLA | 4.2 | −4.4 | 2.1 | 3.4 |
| % Change in 2,6-NDA | 3.1 | −3.2 | 1.3 | 1.3 |

TABLE VII

| Conditions |  |
|---|---|
| Reaction Temp., °F. | 408 |
| Reaction Press., PSIG | 311.6 |
| Wt. % Co | 0.19 |
| Co:Mn:Br | 1:3:2 |
| DMN Feed Rate | 4.69 |
| Solvent Ratio | 3.8 |
| HCTP | 0.12 |
| $CO_2$ g moles/hr | 7.55 |
| CO g moles/hr | 2.56 |
| Total CO & $CO_2$ | 10.11 |

TABLE VII-continued

| Reactor Yields | |
|---|---|
| TMLA | 3.69 |
| 2,6-NDA | 92.14 |
| FNA | 0.43 |
| 2-NA | 0.15 |
| Subsequent Oxygen Treatment, Conditions | |
| Temperature, °F. | 385 |
| Gas Rate, SCFH | 12.12 |
| Reactor Yield Following Oxygen Treatment | |
| TMLA | 3.40 |
| 2,6-NDA | 89.79 |
| FNA | 0.28 |
| 2-NA | 0.13 |
| % Change in FNA | −34.9 |
| % Change in TMLA | −7.9 |
| % Change in 2,6-NDA | −2.6 |

TABLE VIII

| | Reactor Yield | | |
|---|---|---|---|
| | Base Case | With Mother Liquor Recycle | Corrected Yield[a] |
| TMLA | 3.41 | 3.81 | 2.59 |
| 2,6-NDA | 94.53 | 93.30 | 92.42 |
| FNA | 0.48 | 0.63 | 0.55 |
| Br-NDA | 0.35 | 0.76 | 0.68 |
| 2-NA | 0.22 | 0.31 | −0.04 |

[a]Yield after subtracting components carried over from mother liquor.

EXAMPLE 8

Table IX lists the product analysis of filter cakes obtained by filtering solid 2,6-naphthalenedicarboxylic acid from the total reactor effluent. These data show that side products present in the total reactor effluent contaminate the desired 2,6-naphthalenedicarboxylic acid when it is isolated and, therefore, confirm that it is essential to eliminate as much as possible the side products produced in the oxidation reaction. These data are from an average of eight continuous oxidation runs as reported in Table VII.

In Examples 9 and 10, the oxidation of 2,6-dimethylnaphthalene to 2,6-naphthalenedicarboxylic acid was conducted in the semi-continuous mode using a one liter titanium pressure reactor equipped with an overhead condenser, stainless steel product receiver, internal cooling coil, agitator, and feed and catalyst lines. During the reaction, analyzers were used to monitor temperature, pressure, and vent gas composition.

In a typical run, the reactor was charged with solvent and catalyst, pressurized, and heated under nitrogen to the initiation temperature. The reaction was started by simultaneously adding compressed air and 2,6-dimethylnaphthalene. The 2,6-dimethylnaphthalene was added as a 50:50 by weight mixture with acetic acid. Typical reaction parameters are as follows: air rate, 0.18 SCFM; pressure, 300 psig; initiation temperature, 350° F.; reaction temperature, 405° F.; agitator speed 1200 rpm; feed pump rate, 2 ml/minute. The reaction time was 125 minutes and the final weight ratio of solvent to 2,6-dimethylnaphthalene was 5:1.

The recycled mother liquor used for runs 20 through 23 was from a prior semi-continuous oxidation of 2,6-dimethylnaphthalene and had the following approximate composition:

| Component: | Weight Percent |
|---|---|
| 2,6-NDA | 0.46 |
| FNA | 0.005 |
| Br-NDA | 0.016 |
| TMLA | 0.43 |
| Co | 0.07 |
| Mn | 0.19 |
| Bromine | 0.93 |
| Water | 30.5 |

TABLE IX

| Reactor Yield[a] | |
|---|---|
| TMLA | 3.69 |
| 2,6-NDA | 92.14 |
| FNA | 0.43 |
| 2-NA | 0.15 |
| Filtered Cake Analysis | |
| TMLA | 2.85 |
| 2,6-NDA | 92.83 |
| FNA | 0.33 |
| 2-NA | 0.04 |

[a]Br-NDA not measured.

EXAMPLE 9

Table X provides the results from a series of semi-continuous oxidation runs wherein mother liquor from a prior semi-continuous oxidation run was used to supply 20 or 25 weight percent of the cobalt used for the oxidation. The mother liquor recycled contained 30 weight percent water.

These data demonstrate that 20 percent recycle (i.e. Runs 20 and 21 compared to Runs 18 and 19) of a mother liquor containing 30 weight percent water can be used. However, the levels of Br-NDA are elevated with the recycle.

When the mother liquor was recycled to provide for 25 weight percent of the added cobalt (i.e. Run 22), the levels of FNA and TMLA increased substantially. The level of Br-NDA also increased substantially. This increase in impurities is primarily due to the initial elevated water levels in the reaction mixture from the mother liquor (i.e. 15 weight percent based on acetic acid).

In Run 23, acetic anhydride was used to eliminate water from the recycled mother liquor. The levels of impurities in the product decreased to levels similar to the Runs 18 and 19 where no recycle was used. However, the level of Br-NDA was still elevated. This run demonstrates that water in the recycled mother liquor is detrimental to the oxidation reaction where mother liquor is used as a source of the catalyst metals.

TABLE X

| | Run 18 | Run 19 | Run 20 | Run 21 | Run 22 | Run 23 |
|---|---|---|---|---|---|---|
| Fresh Feed[a] | | | | | | |
| Acetic acid, grams | 480 | 480 | 320 | 320 | 240 | 82 |
| Cobalt | 0.12 | 0.12 | 0.10 | 0.10 | 0.09 | 0.09 |
| Mn:Co:Br | 3:1:2 | 3:1:2 | 3:1:2.2 | 3:1:2.2 | 3:1:2.2 | 3:1:2.2 |
| Water, wt % | 5 | 5 | 0 | 0 | 0 | 0 |
| Recycled Catalyst[b] | | | | | | |
| Mother Liquor Recycle, % | 0 | 0 | 20 | 20 | 25 | 25 |
| Cobalt | 0 | 0 | 0.02 | 0.02 | 0.03 | 0.03 |
| Mn:Co:Br | — | — | 2.8:1:1 | 2.8:1:1 | 2.8:1:1 | 2.8:1:1 |
| Recycled ML, grams | 0 | 0 | 160 | 160 | 240 | 240 |

TABLE X-continued

| | Run 18 | Run 19 | Run 20 | Run 21 | Run 22 | Run 23 |
|---|---|---|---|---|---|---|
| Water in ML, wt % | 0 | 0 | 30 | 30 | 30 | 30 |
| TMLA in ML, wt % | 0 | 0 | 0.43 | 0.43 | 0.43 | 0.43 |
| Acetic Anhyd. in ML, grams | 0 | 0 | 0 | 0 | 0 | 241 |
| Net Water in Recycled ML, wt % Total[c] | 0 | 0 | 30 | 30 | 30 | 8 |
| Cobalt | 0.12 | 0.12 | 0.12 | 0.12 | 0.12 | 0.12 |
| Mn:Co:Br | 3:1:2 | 3:1:2 | 3:1:2 | 3:1:2 | 3:1:2 | 3:1:2 |
| Water, wt. % | 5 | 5 | 10 | 10 | 15 | 4 |
| Reactor Yields, mole %[d] | | | | | | |
| 2,6-NDA | 95 | 101 | 89 | 87 | 97 | 87 |
| TMLA[e] | 3.9 | 3.8 | 4.1 | 4.2 | 5.7 | 4.0 |
| FNA | 0.26 | 0.28 | 0.25 | 0.26 | 0.42 | 0.21 |
| Br-NDA | 0.20 | 0.30 | 0.70 | 0.76 | 1.18 | 0.71 |
| Carbon Dioxide[f] | 3.65 | 3.16 | 2.13 | 2.12 | 1.84 | 2.04 |
| Carbon Monoxide[f] | 0.95 | 0.88 | 0.68 | 0.62 | 0.52 | 0.64 |
| Final Water in Reactor Effluent, wt % | 12.1 | 11.6 | 12.5 | 13.3 | 14.4 | 11.8 |

[a] These are the quantities of fresh feed reaction components charged to the reactor. Cobalt is in weight percent elemental cobalt based on total acetic acid charged to reactor. Mn:Co:Br is the atom ratio of catalyst components. Water is weight percent of acetic acid charged.
[b] These are the quantities of recycled reaction components charged to reactor. Cobalt is in weight percent elemental cobalt based on total acetic acid charged to reactor. Mn:Co:Br is the atom ratio of catalyst components. ML is the mother liquor obtained from a prior semicontinuous oxidation run.
[c] Total based on (a) and (b) as described above.
[d] Total reactor effluent yields based on 2,6-dimethylnaphthalene charged. Values for 2,6-NDA are +/− 5%.
[e] Since recycled mother liquor (ML) contained TMLA, the apparent TMLA yield was increased by 0.4 mole % for Runs 20 and 21 and 0.7 mole % for Runs 22 and 23.
[f] Yield in mole % assuming only one third of CO and $CO_2$ is from 2,6-dimethylnaphthalene.

EXAMPLE 10

Table XI provides data from the semi-continuous oxidation of 2,6-dimethylnaphthalene using cobalt and manganeses oxalate salts as a part of or all of the oxidation catalyst metals. The oxalate salts used in Runs 24 and 25 were obtained by precipitating cobalt and manganese from actual mother liquor from a prior semi-continuous oxidation run. The oxalate salts used for Runs 26 and 27 were purchased from Johnson Matthey, Inc., Seabrook, N.H. or GFS Chemicals, Powell, Ohio. These data demonstrate that oxalate salts of cobalt and manganese are active oxidation catalysts.

The recovery of the oxalate salts from reaction mixture mother liquor was conducted as follows:

Approximately 0.92 mole of oxalic acid per mole of cobalt and manganese catalyst metals was added to a sample of mother liquor. The mixture was heated to reflux for about 15 minutes. The solids formed were separated by filtration, washed with hot acetic acid and dried.

EXAMPLE 11

Table XI, Runs 28, and 29, provides data demonstrating the effect of trimellitic acid on the semi-continuous oxidation reaction. When the reaction mixture was spiked with trimellitic acid (5 grams for Run 28 and 10 grams for Run 29) the oxidation reaction was affected. For Run 28, the amounts of 2,6-NDA, FNA and Br-NDA produced were equivalent to the base case runs (Runs 18 and 19 in Table X), however, TMLA levels were elevated by about 30%, i.e. if the added TMLA did not affect the reaction, the yield of TMLA would have been 7.5%, 4% produced in the reaction and 3.5% corresponding to the 5 grams of TMLA added to the reaction. For Run 29, the 10 grams of added TMLA severely inhibited the reaction. For Run 28, the TMLA: catalyst metal ratio was about 0.5, for Run 29, about 1. Therefore, mole ratios of TMLA: catalyst metals above about 1.0 severely inhibit the oxidation reaction.

TABLE XI

| | Run 24 | Run 25 | Run 26 | Run 27 | Run 28 | Run 29 |
|---|---|---|---|---|---|---|
| % Cat. Metals Recycled as Oxalates | 50 | 50 | 50 | 100 | 0 | 0 |
| Fresh Feed[a] | | | | | | |
| Acetic acid, grams | 480 | 480 | 480 | 480 | 480 | 480 |
| Cobalt | 0.06 | 0.06 | 0.06 | 0 | 0.12 | 0.12 |
| Mn:Co:Br | 3:1:4 | 3:1:4 | 3:1:4 | 0:0:2 | 3:1:2 | 3:1:2 |
| Water, wt % | 5 | 5 | 5 | 5 | 5 | 5 |
| Co:TMLA, atom ratio[b] | — | — | — | — | 1:1.9 | 1:3.8 |
| Recycled Catalyst[c] | | | | | | |
| Cobalt | 0.05 | 0.05 | 0.06 | 0.12 | 0 | 0 |
| Mn:Co | 3:1 | 3:1 | 3:1 | 3:1 | 0 | 0 |
| Total[d] | | | | | | |
| Cobalt | 0.11 | 0.11 | 0.12 | 0.12 | 0.12 | 0.12 |
| Co:Mn:Br | 3:1:2 | 3:1:2 | 3:1:2 | 3:1:2 | 3:1:2 | 3:1:2 |
| Reactor Yields, mole %[e] | | | | | | |
| 2,6-NDA | 96 | 86 | 96 | 101 | 91 | 48 |
| TMLA | 4.0 | 3.7 | 3.8 | 4.6 | 8.7 | 11 |
| FNA | 0.27 | 0.26 | 0.20 | 0.29 | 0.20 | 0.58 |
| Br-NDA | 0.42 | 0.44 | 0.34 | 0.50 | 0.24 | 0.20 |
| Carbon Dioxide[f] | 2.82 | 2.67 | 2.48 | 2.40 | 2.20 | 1.28 |
| Carbon Monoxide[f] | 0.81 | 0.79 | 0.75 | 0.62 | 0.66 | 0.30 |
| Final Water in Reactor Effluent | 10.6 | 10.3 | 10.2 | 9.8 | 10.3 | 7.33 |

[a] See footnote as in Table X
[b] TMLA was spiked into the reactor for runs 28 and 29.
[c] Cobalt is weight percent elemental cobalt based on total acetic acid charged to reactor. Mn:Co is the atom ratio of catalyst metals.
[d] total based on a and c above.
[e] See footnote d in Table X.
[f] See footnote f in Table X.

EXAMPLE 12

Table XII provides the results from treating oxidation mother liquor with varying amounts of oxalic acid. These data demonstrate that mole ratios of oxalic acid to cobalt and manganese of 0.6 to 2.1 are adequate for recovery of the cobalt and manganese as their oxalic acid complexes. These data also demonstrate that the oxalic acid precipitation leaves most of the undesirable TMLA in the mother liquor.

For tests A and D in Table XII, concentrated mother liquor containing 0.19 wt. % Co, 0.51 wt. % Mn, 0.32 wt. % Br, 2.93 wt. % TMLA and 12.1 wt. % water was used for the precipitation tests. For tests B and C in Table XII, concentrated mother liquor containing 0.29% Co, 0.78 wt. % Mn, 0.46 Wt. % Br, 0.030 Wt. % Fe, and 12.1 wt. % water was used. Atmospheric distillation was used to concentrate the mother liquor. The oxalic acid complexes were prepared by heating the concentrated mother liquor with the appropriate amount of oxalic acid at 90°–100° C. for 15 minutes followed by filtering the precipitated oxalic acid catalyst metal complexes. Iron (Fe) is a typical corrosion metal found in mother liquor.

TABLE XII

|  | Test | | | |
|---|---|---|---|---|
|  | A | B | C | D |
| Mole Ratio of Oxalic Acid to Total Co and Mn | 0.6 | 0.85 | 2.1 | 3.0 |
| Analysis of Oxalate Precipitate | | | | |
| Co Recovery, % | 100 | 100 | 100 | 100 |
| Mn Recovery, % | 61 | 95 | 99 | 106 |
| Br Recovery, % | 19 | 22 | 10 | 16 |
| Fe Recovery, % | NM | 66 | 66 | NM |
| Analysis of Filtrate | | | | |
| Co Recovery, % | 11 | 0 | 0 | 1 |
| Mn Recovery, % | 57 | 12 | 1 | 10 |
| Br Recovery, % | 98 | 75 | 75 | 60 |
| TMLA Recovery, % | 83 | 67 | 73 | 60 |
| Fe Recovery, % | NM | NM | NM | NM |

NM = not measured

Having described the invention, that which is claimed is:

1. A process for producing 2,6-naphthalenedicarboxylic acid by the liquid phase oxidation of 2,6-dimethylnaphthalene, comprising:
   (a) continuously adding to a reaction zone the oxidation reaction components comprising 2,6-dimethylnaphthalene, a source of molecular oxygen, a solvent comprising an aliphatic monocarboxylic acid, and a catalyst comprising cobalt, manganese and bromine components, wherein the weight ratio of monocarboxylic acid solvent to 2,6-dimethylnaphthalene is about 2:1 to about 12:1, the atom ratio of manganese to cobalt is about 5:1 to about 0.3:1, the atom ratio of bromine to the total of cobalt and manganese is about 0.3:1 to about 0.8:1, and the total of cobalt and manganese, calculated as elemental cobalt and manganese, is at least about 0.40 weight percent based on the weight of solvent added to the reaction zone;
   (b) maintaining the contents of the reaction zone at a temperature of about 370° F. to about 420° F., and at a pressure of from about 0.1 atmosphere absolute to about 35 atmospheres absolute, thereby oxidizing the 2,6-dimethylnaphthalene to 2,6-naphthalenedicarboxylic acid; and
   (c) continuously withdrawing from the reaction zone a product mixture comprising 2,6-naphthalenedicarboxylic acid.

2. The process of claim 1 wherein the monocarboxylic acid solvent is acetic acid.

3. The process of claim 2 wherein the weight ratio of acetic acid to 2,6-dimethylnaphthalene is about 2:1 to about 6:1.

4. The process of claim 1 wherein the source of molecular oxygen is air.

5. The process of claim 1 wherein the temperature is about 380° F. to about 415° F.

6. The process of claim 1 wherein the total of cobalt and manganese, calculated as elemental cobalt and manganese, is at least about 0.50 weight percent based on the weight of solvent added to the reaction zone.

7. The process of claim 1 wherein the total of cobalt and manganese, calculated as elemental cobalt and manganese, is at least about 0.70 weight percent based on the weight of solvent added to the reaction zone.

8. The process of claim 1 wherein the atom ratio of bromine to the total of cobalt and manganese is about 0.4:1 to about 0.7:1.

9. The process of claim 1 wherein the atom ratio of manganese to cobalt is about 4:0:1 to about 0.5:1.

10. The process of claim 1 wherein the contents of the reaction zone is about 1 to about 10 weight percent water.

11. The process of claim 1 wherein the rate at which the 2,6-dimethylnaphthalene is added to the reaction zone together with the volume of solvent comprising an aliphatic monocarboxylic acid in the reaction zone provide for a hydrocarbon throughput value in the range of about 0.02 to about 0.20 pound moles of 2,6-dimethylnaphthalene per cubic foot of reactor solvent per hour.

12. The process of claim 11 wherein the hydrocarbon throughput value is in the range of about 0.04 to about 0.16.

13. The process of claim 1 further comprising contacting the 2,6-naphthalenedicarboxylic acid withdrawn from the reaction zone at an elevated temperature with a gas containing molecular oxygen.

14. The process of claim 13 wherein the contacting comprises reacting the product mixture withdrawn from the reaction zone with a gas containing molecular oxygen at a temperature in the range of about 350° F. to about 450° F.

15. The process of claim 13 wherein the contacting comprises partitioning 2,6-naphthalenedicarboxylic acid from the reaction mixture, suspending the separated 2,6-naphthalenedicarboxylic acid in a solvent, and contacting the suspended 2,6-naphthalenedicarboxylic acid with a gas containing molecular oxygen wherein the suspension is at a temperature in the range of about 200° F. to about 450° F.

16. A process for recycling 2,6-dimethylnaphthalene oxidation reaction mother liquor comprising cobalt and manganese catalyst components, water, and trimellitic acid to an oxidation reaction mixture comprising cobalt, manganese and bromine catalyst components and used for the liquid phase oxidation of 2,6-dimethylnaphthalene to 2,6-naphthalenedicarboxylic acid, comprising: adding a portion of the mother liquor to the oxidation reaction mixture so that the oxidation reaction mixture contains less than about 15 weight percent water and the ratio of gram moles of trimellitic acid to total gram atoms of cobalt and manganese in the oxidation reaction mixture is less than about 1.0.

17. The process of claim 16 wherein the oxidation reaction mixture contains less than about 10 weight percent water.

18. The process of claim 16 wherein the ratio of gram moles of trimellitic acid to total gram atoms of cobalt and manganese is less than about 0.5.

19. A process for recovering cobalt and manganese oxidation catalyst metals from oxidation reaction mother liquor formed during the oxidation of 2,6-dimethylnaphthalene to 2,6-naphthalenedicarboxylic acid, comprising contacting the oxidation mother liquor with about 3.0 to about 0.6 gram moles of a source of oxalic acid per gram atom of the total of cobalt and manganese contained in the mother liquor, precipitating an insoluble complex formed by the reaction of the oxalic acid with the cobalt and manganese oxidation catalyst metals, and recovering the insoluble complex.

20. The process of claim 19 further comprising using the recovered insoluble complex formed by the reaction of oxalic acid with cobalt and manganese as a source of catalyst for the liquid phase oxidation of 2,6-dimethylnaphthalene to 2,6-naphthalenedicarboxylic acid.

21. A process of recycling 2,6-dimethylnaphthalene oxidation reaction mother liquor comprising cobalt and manganese catalyst components, water and an aliphatic monocarboxylic acid solvent to an oxidation reaction mixture comprising 2,6-dimethylnaphthalene, aliphatic monocarboxylic acid solvent and a catalyst mixture comprising cobalt, manganese and bromine components, which process comprises adding the oxidation reaction mother liquor to the oxidation reaction mixture while removing from the oxidation reaction mixture a vaporous mixture comprising water and monocarboxylic acid solvent, and returning to the reaction mixture aliphatic monocarboxylic acid solvent containing less water than that removed as a vapor.

* * * * *